United States Patent [19]

Lago et al.

[11] Patent Number: 5,610,112
[45] Date of Patent: *Mar. 11, 1997

[54] METHOD FOR MODIFYING A CATALYST

[75] Inventors: Rudolph M. Lago, Yardley, Pa.; David O. Marler, Deptford, N.J.; Sharon B. McCullen, Newtown, Pa.

[73] Assignee: Mobil Oil Corporation, Fairfax, Va.

[ * ] Notice: The term of this patent shall not extend beyond the expiration date of Pat. No. 5,476,823.

[21] Appl. No.: 264,287

[22] Filed: Jun. 23, 1994

Related U.S. Application Data

[62] Division of Ser. No. 42,431, Apr. 5, 1993, Pat. No. 5,349,144.

[51] Int. Cl.$^6$ .......................................... B01J 29/06
[52] U.S. Cl. ................... 502/63; 502/64; 502/69; 502/71; 502/77; 502/85
[58] Field of Search .................. 502/63, 64, 69, 502/71, 77, 85

[56] References Cited

U.S. PATENT DOCUMENTS

| | | | |
|---|---|---|---|
| 4,080,284 | 3/1978 | Mitchell | 208/111 |
| 4,402,867 | 9/1983 | Rodewald | 252/455 Z |
| 5,321,183 | 6/1994 | Chang et al. | 585/475 |
| 5,403,800 | 4/1995 | Beck et al. | 502/64 |
| 5,476,823 | 12/1995 | Beck et al. | 502/60 |

*Primary Examiner*—Shrive Beck
*Assistant Examiner*—Timothy H. Meeks
*Attorney, Agent, or Firm*—Malcolm D. Keen; Peter W. Roberts

[57] ABSTRACT

A process for shape selective hydrocarbon conversion involves contacting a hydrocarbon feedsteam under conversion conditions with a modified catalytic molecular sieve which has been modified by being pre-selectivated with a first silicon source, then steamed. The feedstream may also contain a second silicon source which is a high efficiency para-xylene selectivating agent. The method for modifying the molecular sieve is also described.

12 Claims, No Drawings

METHOD FOR MODIFYING A CATALYST

CROSS-REFERENCE TO RELATED APPLICATION

This application is a division of U.S. application Ser. No. 08/042,431, filed Apr. 5, 1993, now U.S. Pat. No. 5,349,144.

BACKGROUND OF THE INVENTION

1. Field of the Invention

The present invention is directed to a shape selective hydrocarbon conversion process over a modified catalyst. The invention is also directed to the modified catalyst and method for modifying the catalyst by pre-selectivating with first silicon source followed by steam treatment.

2. Description of the Prior Art

The term shape-selective catalysis describes unexpected catalytic selectivities in zeolites. The principles behind shape selective catalysis have been reviewed extensively, e.g. by N. Y. Chen, W. E. Garwood and F. G. Dwyer, "Shape Selective Catalysis in Industrial Applications, 36, Marcel Dekker, Inc. (1989). Within a zeolite pore, hydrocarbon conversion reactions such as paraffin isomerization, olefin skeletal or double bond isomerization, oligomerization and aromatic disproportionation, alkylation or transalkylation reactions are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. A final type of selectivity results from configurational diffusion where the dimensions of the molecule approach that of the zeolite pore system. A small change in dimensions of the molecule or the zeolite pore can result in large diffusion changes leading to different product distributions. This type of shape selective catalysis is demonstrated, for example, in toluene selective disproportionation to p-xylene. The production of para-xylene is typically performed by methylation or disproportionation of toluene over a catalyst under conversion conditions. Examples are the reaction of toluene with methanol as described by Chen et al., J. Amer. Chem. Sec. 1979, 101, 6783, and toluene disproportionation, as described by Pines in "The Chemistry of Catalytic Hydrocarbon Conversions", Academic Press, N.Y , 1981, p. 72. Such methods typically result in the production of a mixture including para-xylene, ortho-xylene, and meta-xylene. Depending upon the para-selectivity of the catalyst and the reaction conditions, different percentages of para-xylene are obtained. The yield, i.e., the amount of feedstock actually converted to xylene, is also affected by the catalyst and the reaction conditions. The equilibrium reaction for the conversion of toluene to xylene and benzene proceeds as follows:

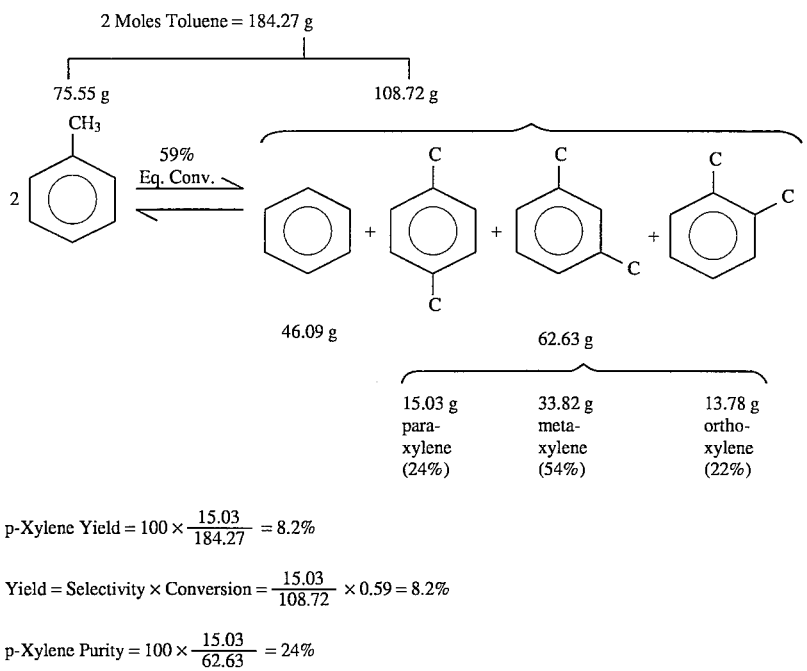

One method for increasing para-selectivity of zeolite catalysts is to modify the catalyst by treatment with a "selectivating agents". For example, U.S. Pat. Nos. 4,950,835, 4,927,979, 4,465,886, 4,477,583, 4,379,761, 4,145,315, 4,127,616, 4,100,215, 4,090,981, 4,060,568 and 3,698,157 disclose specific methods for contacting a catalyst with a modifying compound containing silicon.

U.S. Pat. No. 4,548,914 describes another modification method involving impregnating catalysts with difficultly reducible oxides such as those of magnesium, calcium and/or phosphorus followed by treatment with water vapor to improve paraselectivity.

Steaming has been used in the preparation of zeolite catalysts to modify the alpha or improve stability. For example, U.S. Pat. No. 4,559,314 describes steaming a zeolite/binder composite at 200°–500° C. for at least an hour to enhance activity by raising the alpha. U.S. Pat. No. 4,522,929 describes presteaming a fresh zeolite catalyst so that the alpha activity first rises then falls to the level of the fresh unsteamed catalyst, producing a stable catalyst which may be used in xylene isomerization. U.S. Pat. No. 4,443, 554 describes steaming inactive zeolites (Na ZSM-5) to increase alpha activity. U.S. Pat. No. 4,487,843 describes contacting a zeolite with steam prior to loading with a Group IIIB metal.

There has been no suggestion, however, to steam treat silicon pre-selectivated catalysts to enhance shape-selectivity. It has now been found that pre-selectivation treatment followed by steam treatment of a molecular sieve catalyst provides unexpectedly better results in shape selective hydrocarbon conversions than pre-selectivation alone or steam treatment alone. Furthermore, steaming alone has been found to be detrimental in the context of the present invention.

Accordingly, it is an object of the invention to improve selectivity in catalytic molecular sieves thereby improving shape selectivity in hydrocarbon conversion processes over the molecular sieves.

SUMMARY OF THE INVENTION

The invention is a process for a shape selective hydrocarbon conversion by contacting a feed stream comprising the hydrocarbon, under conversion conditions, with a modified catalytic molecular sieve which has been modified by being pre-selectivated with a first silicon source and treated with steam after it has been pre-selectivated.

The invention is also a process for disproportionation of toluene into xylene which comprises contacting a reaction stream comprising toluene, at reaction conditions for converting toluene to xylene, with a catalytic molecular sieve having an initial Constraint Index of 1 to 12 which has been modified by being pre-selectivated with a first silicon-containing compound, calcined and steamed. The stream may also contain a second silicon source which is a high efficiency para-xylene selectivating agent to provide a single-pass para-xylene product purity relative to all xylene product, of at least about 90% with at least about 15% toluene conversion.

The invention is also a method for modifying a catalytic molecular sieve which includes pre-selectivating the molecular sieve with a first silicon-containing compound, calcining and steaming. The pre-selectivated, calcined, steamed molecular sieve may be subsequently contacted with a mixture of a second silicon source which is a high-efficiency para-xylene selectivating agent and toluene at reaction conditions for converting toluene to xylene to provide a catalyst with greatly enhanced paraselectivity.

The invention is also the catalyst modified by this method.

Advantageously, the modified, steamed catalyst has enhanced shape selectivity for hydrocarbon conversions. Accordingly, the disproportionation process of the invention has an increased toluene disproportionation rate constant with increased selectivity for p-xylene.

DETAILED DESCRIPTION OF THE INVENTION

The present invention is useful in shape selective hydrocarbon conversion reactions, for example, in converting various aromatics such as toluene to commercially useful para-substituted benzenes, such as para-xylene.

The catalytic molecular sieves useful herein have a Constraint Index from about 1 to about 12 and include intermediate pore zeolites. Zeolites which conform to the specified values of Constraint Index for intermediate pore zeolites include ZSM-5, ZSM-11, ZSM-5/ZSM-11 intermediate, ZSM-12, ZSM-21, ZSM-22, ZSM-23, ZSM-35, ZSM-48, ZSM-50, ZSM-57 and Zeolite Beta which are described, for example, in U.S. Pat. Nos. 3,702,886 and Re. No. 29,949, 3,709,979, 3,832,449, 4,046,859, 4,556,447, 4,076,842, 4,016,245, 4,229,424, 4,397,827, 4,046,859, 3,308,069 and Re. 28,341 and EP 127,399 to which reference is made for details of these zeolites. MCM-22, described in U.S. Pat. No. 4,973,784, is also useful herein.

A zeolite incorporated with a binder or in unbound form, is treated with a first silicon source. This first silicon treatment will be called pre-selectivation. In pre-selectivation, the silicon compound is deposited on the external surface of the catalyst by any suitable method. For example, the silicon may be dissolved in a solvent, mixed with the catalyst, and then dried. The silicon compound employed may be in the form of a solution, a liquid or a gas under the conditions of contact with a zeolite. Examples of methods of depositing silicon on the surface of the zeolite are found in U.S. Pat. Nos. 4,090,981, 4,127,616, 4,465,886 and 4,477, 583 to Rodewald, which are incorporated by reference herein. The deposited silicon compound extensively covers the surface and resides substantially exclusively on the external surface of the molecular sieve.

The first silicon-containing compounds which are silicon sources for the pre-selectivation include alkoxy silanes, silanes and organoamine silane polymers and also included are silicones which are the high efficiency, p-xylene selectivating agents discussed below which are also used as second silicon sources for trim selectivation. Preferred silicon containing compounds for pre-selectivation include $Si(OR)_4$ wherein $R=CH_3$, $C_2H_5$ or $C_3H_7$; or a silicone polymer $(SiO(R')_2)_n$ wherein $R'$=alkyl of $C_{1-10}$, aryl of $C_{6-10}$, or hydroxide and n is greater than 10 and less than 1000; or an organoamine silane polymer where the organoamine is —$N(CH_3)_3$, —$N(C_2H_5)_3$ or —$N(C_3H_7)_3$. The molecular sieve may be contacted with silicon-containing compound at a molecular sieve/silicon compound weight ratio of about 100/1 to about 1/100.

Following deposition of the first silicon-containing compound, the catalyst is calcined. For example, the catalyst may be calcined in an oxygen-containing atmosphere, preferably air, at a rate of 0.2° to 5° C./minute to a temperature greater 300° C. but below a temperature at which the crystallinity of the zeolite is adversely affected. Generally, such temperature will be below 600° C. Preferably the temperature of calcination is within the approximate range of 350° to 550° C. The product is maintained at the calcination temperature usually for 1 to 24 hours.

After pre-selectivation and calcining, the catalyst is subjected to steam treatment at a temperature of from about 200° C. to about 538° C., preferably about 280° C. to about 400° C. with from about 5% to about 100% steam at a pressure of from about 0.1 to about 50 psig, preferably from about 50% to about 100% steam, for about two to about twelve hours, preferably from about three to about six hours.

The pre-selectivated molecular sieve catalyst, with or without binder, shows improved selectivity after steaming. If the catalyst is not pre-selectivated before steaming or if the catalyst is pre-selectivated without steaming, as shown in the examples below, the same improvement in selectivity does not occur. Indeed, steaming alone can be detrimental.

Shape Selective Conversions

Zeolites modified in accordance with the invention are generally useful as catalysts in shape selective hydrocarbon conversion processes including cracking reactions involving dewaxing of hydrocarbon feedstocks; isomerization of alkylaromatics; oligomerization of olefins to form gasoline, distillate, lube oils or chemicals; alkylation of aromatics; transalkylation of alkylaromatics; conversion of aromatics to dialkyl-substituted benzene; conversion of oxygenates to hydrocarbons; rearrangement of oxygenates; and conversion of light paraffins and olefins to aromatics.

Dewaxing

The subject catalysts have good cracking and hydrocracking activity and may be used to convert paraffins from high to low molecular weight substances in dewaxing processes. The catalysts of the invention may be used in processes such as those described, for example, in U.S. Pat. Nos. 3,700,585, Re. 28,398, 3,968,024 and 4,181,598 which are incorporated herein by references. The term dewaxing means the removal of those hydrocarbons which will readily solidify (waxes) from petroleum stocks. Hydrocarbon feeds which can be treated include lubricating oil stocks as well as those which have a freeze point or pour point problem, i.e., petroleum stocks boiling above 350° F. The dewaxing can be carried out at either cracking or hydrocracking conditions.

In U.S. Pat. No. 3,700,585 and U.S. Pat. No. Re. 28,398 to Chen et al., typical cracking conditions include a liquid hourly space velocity (LHSV) between about 0.5 and 200, a temperature between about 280° C. (550° F.) and 590° C. (1100° F.), a pressure between about subatmospheric and several hundred atmospheric over ZSM-5 type catalysts. Typical hydrocracking conditions include a liquid hourly space velocity between about 0.1 and 10, a temperature between about 340° C. (650° F.) and 538° (1000° F.), a pressure between about 100 and 3000 psig, and a hydrogen to hydrocarbon mole ratio between about one and 20. U.S. Pat. No. 3,968,024 describes similar conversion using ZSM-5 of small crystal size. U.S. Pat. No. 4,181,598 describes shape selective cracking to produce lubes.

Isomerization of alkylaromatics

The modified catalysts of the invention are also advantageously used in the isomerization of alkylaromatics in conversion reactions of the type described, for example, in U.S. Pat. Nos. 3,856,872, 3,856,873, Re. 30,157, 4,101,595, 4,101,597, 4,312,790, Re. 31,919 and 4,224,141 which are herein incorporated by reference.

In U.S. Pat. No. 3,856,872 to Morrison, there is described a process for converting $C_8$ aromatics xylene and ethylbenzene to para-xylene (octafining) at a temperature of 550° F. (288° C.) to 900° F. (482° C.), a pressure of 150 to 300 psig, and a liquid hour space velocity (LHSV) of 1 to 200 over an acid form catalyst containing metal such as platinum or nickel and hydrogen.

In U.S. Pat. No. 3,856,873 to Burress, mixtures of $C_8$ aromatic hydrocarbons are isomerized to para-xylene by contact in vapor phase with zeolite at a temperature of 500° F. (260° C.) to 1000° F. (538° C.), a pressure of 0 (atmospheric) to 1,000 psig, and a WHSV of 0.5 to 250 with no added hydrogen. The catalyst is an acid ZSM-5, ZSM-12 or ZSM-21.

U.S. Pat. No. 4,101,595 to Chen et al. describes the production of para-xylene from aromatics of 8 to 10 carbons over a dual function catalyst with a shape selective acid catalyzed step at a temperature of 650° F. (343° C.) to 1000° F. (538° C.), a pressure of 50 to 500 psig, a LHSV of 0.1 to 100 and a molar of hydrogen/hydrocarbon of 0.1 to 15. The acid form catalyst has a constraint index of 1 to 12, a silica/alumina ratio of at least 12, a crystal density of not less than 1.6 g/cc, may be pre-coked, and includes Group VIII noble metal.

In U.S. Pat. No. 4,101,597 to Breckenridge, a $C_8$ feed is first isomerized at 550° F. (288° C.) to 700° F. (371° C.) over a zeolite having a constraint index of 1 to 12, a silica/alumina ratio of at least 12 and containing a metal having a hydrogenation/dehydrogenation function. A $C^{9+}$ fraction produced during isomerization of $C_8$ is separated from the other isomerization products, blended with hydrogen and toluene and contacted with a porous, acidic catalyst such as ZSM-5 at 750° F. (399° C.) to 900° F. (482° C.). The catalyst has a constraint index of 1 to 12, a silica/alumina ratio of at least 12, and a metal providing hydrogenation/dehydrogenation function.

In U.S. Pat. No. 4,224,141 to Morrison, $C_8$ aromatics are isomerized to benzene, toluene and xylenes over a ZSM-5 which is reduced in activity by dilution with inert matrix, steaming or thermal treatment, very high silica/alumina ratio, base exchange with alkali metal, coking or the like. The conversion is at a temperature of 800° F. (427° C.) to 1000° F. (538° C.) in a low pressure isomerization unit at a pressure only sufficient to overcome pressure drop through downstream processing equipment, e.g. below 100 psig, and a WHSV of 1 to 200.

In U.S. Pat. No. 4,312,790 and Re. 31,919 to Butter et al., a zeolite is incorporated with noble metal subsequent to zeolite crystallization but prior to catalyst extrusion. The catalyst is used for xylene isomerization at a temperature of 500° F. (260° C.) to 1000° F. (540° C.), a pressure between 50 and 1000 psig, a WHSV of 1 to 50 and a hydrogen/hydrocarbon mole ratio of 1 to 20.

Conversion of Oxygenates to Hydrocarbons

U.S. Pat. No. 4,476,330 to Kerr et al. describes the conversion of aliphatic oxygenates to a higher molecular weight compound by contacting with a zeolite having a silica/alumina ratio substantially greater than 10 at a temperature of 70° F. (21° C.) to 1400° F. (760° C.). The feeds include lower aliphatic organic oxygenates up to $C_6$, acetals, ketals, acid halides, alcohols, carboxylic acids, aldehydes, acid anhydrides, epoxides, ethers, esters, hemiacetals, gem diols, hydroxy acids, ketones, ketenes, lactones, peracids, peroxides, sugars, and especially alcohols, ethers and esters.

Oligomerization of olefins

The modified catalysts of the invention are advantageously used in the oligomerization of olefins to form gasoline, distillate, lube oils or chemicals in conversion reactions of the type described, for example, in U.S. Pat. Nos. 4,517,399, 4,520,221, 4,547,609 and 4,547,613 which are herein incorporated by reference.

U.S. Pat. No. 4,517,399 to Chester et al. describes the conversion of olefins of 3 to 18 carbons, e.g. propylene, to high viscosity, low pour point lubricating oils by contacting with ZSM-5 type zeolites having large crystals of at least two microns. The conversion conditions include a temperature of 350° F. (177° C.) to 650° F. (343° C.) a pressure of 100 to 5000 psig, and a WHSV of 0.1 to 10.

U.S. Pat. No. 4,520,221 to Chen describes the polymerization of olefins of 2 to 8 carbons, e.g. propylene, butylene, to high viscosity lubes, e.g. linear hydrocarbons, over highly siliceous, acidic ZSM-5 type catalysts with surface acidity inactivated by treatment with base, e.g. bulky amines with a cross-section larger than about 5 Angstroms. The conversion involves a one or two stage process with the polymerization of lower olefins to linear materials, e.g. at about 200° C. over a surface poisoned zeolite, and oligomerization of the product over a modified or unmodified catalyst at a temperature of 50°–75° lower than the first stage, e.g. 150° C. Therefore, the temperatures range from 25° C. to 400° C., with a pressure of atmospheric to 1500 psi and a WHSV of 0.04 to 1.0.

U.S. Pat. No. 4,547,609 to Dessau describes a two stage process whereby in the first stage, light olefins of 2 to 6 carbons are oligomerized to gasoline and distillate liquids including aliphatics of 10 to 20 carbons over a zeolite having a crystal size greater than 0.5 micron at conditions including a temperature of 500° F. (260° C.) or higher, e.g. a range of 500° F. (260° C.) to 800° F. (437° C.), a pressure of atmospheric to 2000 psig and a WHSV of 0.1 to 20. In the second stage, the distillate fraction is converted to high viscosity lubes by contact with a zeolite of smaller crystal size under milder conditions of a temperature about 200° F. (100° C.) to 500° F. (260° C.), a pressure of atmospheric to 650 psig, and a WHSV less than one.

U.S. Pat. No. 4,547,613 to Garwood et al. describes converting olefins of 2 to 16 carbons to high viscosity lube oil. A ZSM-5 type catalyst is pre-conditioned by contact with light olefins of 2 to 16 carbons, e.g. propylene at 400° F. (204° C.) to 1000° F. (538° C.), at a pressure of 0 to 100 psig for 1 to 70 hours. Conversion conditions include a temperature of 350° F. (177° C.) to 650° F. (343° C.), a pressure of 400 to 5000 psig and a WHSV of 0.1 to 10. The lube fraction may be subjected to a hydrogenation step to stabilize.

Conversion of aromatics to dialkyl-substituted benzene

The modified zeolite catalysts of the invention are advantageously used in the conversion of aromatics compounds to provide dialkyl-substituted benzene products which are highly enriched in the para-dialkyl substituted benzene isomer. Conversion reactions of this type include aromatics alkylation, transalkylation and disproportionation. Aromatics alkylations in which the catalysts of the invention can be used are described, for example, in U.S. Pat. Nos. 3,755,483, 4,086,287, 4,117,024 and 4,117,026 which are herein incorporated by reference.

As described in U.S. Pat. No. 3,755,483 to Burress, aromatic hydrocarbons such as benzenes, naphthalenes, anthracenes and substituted derivatives thereof, e.g. toluene and xylene, may be alkylated with alkylating agents such as olefins ethylene, propylene, dodecylene, and formaldehyde, alkyl halides, and alkyl alcohols with 1 to 24 carbons under vapor phase conditions including a reactor inlet temperature up to about 900° F. (482° C.), with a reactor bed temperature up to about 1050° F. (566°), at a pressure of about atmospheric to about 3000 psig, a ratio of aromatic/alkylating agent of about 1:1 to about 20:1 and a WHSV of 20 to 3000 over ZSM-12.

As described in U.S. Pat. No. 4,086,287 to Kaeding et al., monoalkylbenzenes having alkyls of 1-2 carbons, such as toluene and ethylbenzene, may be ethylated to produce a para-ethyl derivative, e.g. para-ethyltoluene at a temperature of from about 250° C. to about 600° C., a pressure of 0.1 atmospheres to 100 atmospheres, a weight hourly space velocity (WHSV) of 0.1 to 100, and a ratio of feed/ethylating agent of 1 to 10 over a catalyst having an acid activity, i.e., alpha, of 2 to 5000, modified by precoking or combining with oxides of phosphorus, boron or antimony to attain a catalyst with a xylene sorption capacity greater than 1 g/100 g of zeolite and an ortho xylene sorption time for 30% of said capacity of greater than 10 minutes, where sorption capacity and sorption time are measured at 120° C. and a xylene pressure of 4.5±0.8 mm of mercury.

U.S. Pat. No. 4,117,024 to Kaeding describes a process for the ethylation of toluene or ethylbenzene to produce p-ethyltoluene at a temperature of 350° C. to 550° C., a critical pressure of greater than one atmosphere and less than 400 psig, with hydrogen/ethylene ratio of 0.5 to 10 to reduce aging of the catalyst. The zeolite described in U.S. Pat. No. 4,117,024 has a crystal size greater then one micron, and is modified as the catalyst in U.S. Pat. No. 4,086,287 to attain the sorption capacity described in U.S. Pat. No. 4,086,287.

U.S. Pat. No. 4,117,026 to Haag and Olson describes the production of para-dialkyl benzenes having alkyls of 1 to 4 carbons under conditions which vary according to the feed. When the feed includes monoalkyl substituted benzenes having an alkyl of 1 to 4 carbons, olefins of 2 to 15, or paraffins of 3 to 60 carbons or mixtures thereof, conversion conditions include a temperature of 250° C. to 750°, a pressure of 0.1 to 100 atmospheres and a WHSV of 0.1 to 2000. For the disproportionation of toluene, the conditions include a temperature of 400° C. to 700° C., a pressure of 1 to 100 atmospheres and a WHSV of 1–50. When the feed includes olefins of 2 to 15 carbons including cyclic olefins, the conversion conditions include a temperature of 300° C. to 700° C., a pressure of 1 to 100 atmospheres and a WHSV of 1 to 1000. When the feed includes paraffins of 3 to 60 carbons, conditions include a temperature of 300° C. to 700° C., a pressure of 1 to 100 atmospheres and a WHSV of 0.1 to 100. However for lower paraffins of 3 to 5 carbons, the temperature should be above 400° C. When the feed includes mixed aromatics such as ethylbenzene and toluene, and also optionally olefins of 2 to 20 carbons or paraffins of 5 to 25 carbons, conversion conditions includes a temperature of 250° C. to 500° C. and a pressure greater than 200 psig. In the absence of added aromatics, the olefins and higher paraffins are more reactive and require lower severity of operation, e.g. a temperature of 250° C. to 600° C., preferably 300°–550° C. The catalyst described in U.S. Pat. No. 4,117,026 is modified as in U.S. Pat. No. 4,086,287.

Conversion of light paraffins and olefins to aromatics

The modified catalysts of the invention may also be used in the conversion of light paraffins and olefins to aromatics in processes of the type described, for example, in U.S. Pat. Nos. 3,760,024 and 3,756,942 which are herein incorporated by reference.

U.S. Pat. No. 3,760,024 to Cattanach describes a process for the conversion of paraffins of 2 to 4 carbons and/or olefins to aromatics of 6 to 10 carbons over a ZSM-5 type catalyst with or without hydrogenation/dehydrogenation component. Conversion conditions include a temperature of 100° C. to 650° C., a pressure of 0 to 1,000 psig, a WHSV of 0.1 to 500 and a hydrogen/hydrocarbon ratio of 0 to 20.

U.S. Pat. No. 3,756,942 to Cattanach describes the conversion of paraffins, olefins and naphthenes to aromatics over ZSM-5 type catalysts. If the feed contains at least 35 wt. % olefins, conversion is at 650° F. (363° C.) to 1400° F. (760° C.). If the feed contains less than 35 wt. % olefins, the temperature is 900° F. (482° C.) to 1400° F. (760° C.) with the absence of substantial added hydrogen. For both types of feed, the pressure is atmospheric to 35 atmospheres and the WHSV 1 to 15.

Therefore, the modified catalysts of the present invention are suitable for use in a variety of shape selective hydrocarbon conversion processes including as non-limiting examples, cracking hydrocarbons with reaction conditions including a temperature of from about 300° C. to about 700° C., a pressure of from about 0.1 atmosphere (bar) to about 30 atmospheres and a weight hourly space velocity of from about 0.1 $hr^{-1}$ to about 20 $hr^{-1}$; dehydrogenating hydrocarbon compounds with reaction conditions including a temperature of from about 300° C. to about 700° C., a pressure of from about 0.1 atmosphere to about 10 atmospheres, and a weight hourly space velocity of from about 0.1 to about 20; converting paraffins to aromatics with reaction conditions including a temperature of from about 300° C. to about 700°

C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g. benzene, toluene and xylene, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g. methanol, or ethers, e.g. dimethylether, or mixtures thereof to hydrocarbons including olefins and/or aromatics with reaction conditions including a temperature of from about 275° C. to about 600° C., a pressure of from about 0.5 atmosphere to about 50 atmospheres and a liquid hourly space velocity of from about 0.5 to about 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure from about atmospheric to about 60 atmospheres and a weight hourly space velocity of from about 0.08 to about 20; alkylating aromatic hydrocarbons, e.g. benzene and alkylbenzenes in the presence of an alkylating agent, e.g. olefins, formaldehyde, alkyl halides and alcohols, with reaction conditions including a temperature of from about 250° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; and transalkylkating aromatic hydrocarbons in the presence of polyalkylaromatic hydrocarbons with reaction conditions including a temperature of from about 340° C. to about 500° C., a pressure of from about atmospheric to about 020 atmospheres, a weight hourly space velocity of from about 10 to about 1000 and an aromatic hydrocarbon/polyalkylaromatic hydrocarbon mole ratio of from about 1/1 to about 16/1.

In general, therefore, catalytic conversion conditions over a catalyst comprising the modified zeolite include a temperature of from about 100° C. to about 760° C., a pressure of from about 0.1 atmosphere (bar) to about 200 atmospheres (bar), a weight hourly space velocity of from about 0.08 $hr^{-1}$ to about 2000 $hr^{-1}$ and a hydrogen/organic, e.g. hydrocarbon compound of from 0 to about 100.

Toluene Disproportionation

Toluene Disproportionation will be used as a representative shape selective conversion. A catalyst treated in the manner described herein has a desirable decreased orthoxylene sorption rate parameter and yields a para-selective product in toluene disproportionation.

Diffusion rate constants in toluene disproportionation have been discussed by D. H. Olson and W. O. Haag, "Structure-Selectivity Relationship in Xylene Isomerization and Selective Toluene Disproportionation" Catalytic Materials Relationship Between Structure and Reactivity, ACS Symposium Ser. No. 248 (1984).

In toluene disproportionation, toluene diffuses into the zeolite with a diffusivity $D_T$. The toluene undergoes disproportionation to p-, m-, and o-xylene and benzene at a total rate constant $k_D$:

$$k_D = \frac{D_T}{r^2}$$

The degree of para-selectivity depends on the activity and the diffusion characteristics of the catalyst. The primary product will be rich in the para isomer if initially produced m- and o- xylene diffuse out of the zeolite crystal at a lower rate $(D_{m,o}/r^2)$ than that of their conversion to p-xylene $(k_I)$ and the p-xylene diffusion $(D_p/r^2)$ out of the catalyst $D_m$=diffusion of m-xylene $D_o$=diffusion of o-xylene $D_p$=diffusion of p-xylene r=length of diffusion path (crystal radius)

$k_I$=rate of interconversion via isomerization of xylene isomers yielding secondary xylene product m-xylene and o-xylene.

It is desirable to reduce the $k_I$ thereby reducing the isomerization of p-xylene to o- and m-xylene in a secondary reaction by adjusting $D_{m,o}/r^2$ downward so that $$k_I > \frac{D_{m,o}}{r^2}$$

Thus a para-rich primary product will result. It is therefore apparent that if the o-xylene diffusion $(D_o/r^2)$ can be adjusted downward, the p-xylene product will increase.

Selective Toluene Disproportionation may be carried out under conditions which include a temperature between about 200° C. and about 600° C., a pressure from about 0.1 psig to about 1000 psig, a weight hourly space velocity (WHSV) from about 0.1 $hr^{-1}$ to about 20 $hr^{-1}$ and a hydrogen/hydrocarbon mole ratio from 0 to about 20.

The catalyst may be pre-selectivated ex situ with a first silicon-containing compound as described above, calcined then steamed and optionally trim selectivated with a second silicon-containing compound which is termed a high efficiency para-xylene selectivating agent.

The invention involves the disproportionation of toluene. However, the present invention also applies to other methylation reactions such as those using methylhalides and methylethers. Normally a single pass conversion of a toluene stream results in a product stream which includes dimethylbenzenes having alkyl groups at all locations, i.e., ortho-, meta-, and para-xylenes. Furthermore, the xylenes are known to proceed in a reaction which produces unwanted ethylbenzenes (EB) by the following reaction:

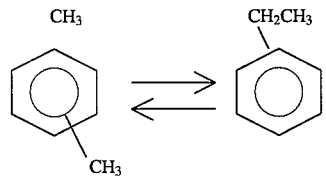

By deposition of platinum on the molecular sieve, the presence of ethylbenzene can be reduced.

As explained in greater detail herein, the present invention provides a process for obtaining p-xylene at toluene conversion rates of at least 15%, preferably at least about 20–25%, with a para-xylene purity of greater than 85%, preferably at least 90%.

The present invention also comprises the regioselective conversion of toluene to para-xylene by methylating toluene in a reaction stream containing a toluene feed with a trim selectivated catalytic molecular sieve which has been pre-selectivated and steamed. The trim selectivation method is described below. As used herein, the term "para-xylene purity" means the percentage of para-xylene in all of the xylene products para-xylene, ortho-xylene, and meta-xylene. Those skilled in the art will appreciate that the proximity of the boiling points of these xylene products necessitates more expensive separation processes whereas para-xylene may be more readily separated from other components in the product stream such as benzene, toluene, and para-ethyltoluene.

As used herein, the term "xylene-conversion product" indicates the total amount of xylenes resulting from the disproportionation reaction. The word "para-xylene" in this term is not intended to limit the scope of the present invention to the production of xylenes since other para-substituted aromatics may be produced.

The invention also comprises a method for the regioselective production of para-xylene by passing a reaction stream which contains an aromatic feedstock, e.g. toluene, in a single pass, over a pre-selectivated, steamed, then trim-selectivated catalytic molecular sieve, the single pass in the presence of hydrogen at reaction conditions suitable to provide para-xylene purity of greater than about 80%, preferably greater than 90%. The product stream may also include small amounts of ortho- and meta-xylene and trace amounts of impurities such as ethylbenzene.

The toluene may be fed simultaneously with a second silicon source which is a high-efficiency selectivating agent and hydrogen at reaction conditions until the desired p-xylene selectivity is attained, whereupon the feed of selectivating agent is discontinued. This co-feeding of selectivating agent with toluene will be termed "trim selectivation". Reaction conditions for this trim-selectivation step generally include a temperature of about 350°–540° C. and a pressure of about atmospheric –5000 psig. The feed is provided to the system at a rate of about 0.1–20 WHSV. The hydrogen is fed at a hydrogen to hydrocarbon molar ratio of about 0.1–20.

The high efficiency para-xylene selectivating agent for trim selectivation preferably comprises a silicon containing compound discussed in greater detail below. For example, organic silicons such as phenylmethyl silicone, dimethyl silicone, and mixtures thereof are suitable. According to one preferred embodiment of the present invention, a silicone containing phenylmethylsilicone and dimethylsilicone groups in a ratio of about 1:1 is co-fed to the system, while the other components, e.g. toluene and hydrogen, are fed in the amounts set forth above. The high-efficiency para-xylene selectivating agent is fed in an amount of about 0.1%–50% of the toluene according to one embodiment. Depending upon the percentage of selectivating agent used, the trim selectivation will last for at least one hour, or about 50–300 hours, most preferably less than 170 hrs.

As used herein, the term "high efficiency, p-xylene selectivating agent" may be used for both trim selectivation and pre-selectivation and is used to indicate substances which will increase the para-selectivity of a catalytic molecular sieve to the stated levels in toluene disproportionation while maintaining commercially acceptable toluene to xylene conversion levels. Such substances include, for example, organic silicon compounds such as phenylmethyl silicone, dimethylsilicone, and blends thereof which have been found to be suitable.

The trim selectivation of the catalyst is preferably performed with a second silicon containing compound which is herein termed a high efficiency, p-xylene selectivating agent. These selectivating agents include silicone compounds which can be characterized by the general formula:

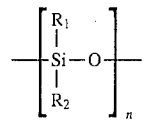

where $R_1$ is hydrogen, fluorine, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropysilicone, polydimethylsilicone, tetrachlorophenylmethyl silicone, tetrachlorophenylethyl silicone, tetrachlorophenylhydrogen silicone, tetrachlorophenylphenyl silicone, methylvinylsilicone and ethylvinylsilicone. The silicone compound need not be linear but may be cyclic as for example hexamethylcyclotrisiloxane, octamethylcyclotetrasiloxane, hexaphenylcyclotrisiloxane and octaphenylcyclotetrasiloxane. Mixtures of these compounds may also be used as well as silicones with other functional groups. Other silicon-containing compounds, such as silanes, may also be utilized.

Preferably, the kinetic diameter of the high efficiency, p-xylene selectivating agent is larger than the zeolite pore diameter, in order to avoid reducing the internal activity of the catalyst.

While not wishing to be bound by theory, it is believed that advantages of the present invention are in part obtained by rendering acid sites on the external surfaces of the catalyst substantially inaccessible to reactants while increasing catalyst tortuosity. Acid sites existing on the external surface of the catalyst are believed to isomerize the para-xylene exiting the catalyst pores back to an equilibrium level with the other two isomers, thereby reducing the amount of para-xylene in the xylenes to only about 24%. By reducing the availability of these acid sites to the para-xylene exiting the pores of the catalyst, the relatively high level of para-xylene can be maintained. It is believed that the high-efficiency, p-xylene selectivity agents of the present invention block or otherwise render these external acid sites unavailable to the para-xylene by chemically modifying said sites.

In line with this theory, it is also believed that the presence of hydrogen in the reaction zone during the trim selectivation is important in order to maintain the desired high yields of para-xylene when a silicone compound is used as the high-efficiency para-xylene selectivating agent. The importance of the hydrogen may be reduced in alternative embodiments by using a high efficiency para-xylene selectivating agent comprising silane or some other compound which effectively renders the isomerizing acid sites on the external surface of the catalyst inaccessible.

One process of the present invention utilizes a high efficiency para-xylene selectivating agent which includes a silicon compound wherein the silicon compound is introduced by co-feeding, for example, at least one silicon compound with the toluene feedstock over a conversion catalyst at reaction conditions until the desired degree of selectivation is achieved, at which time the feed of selectivating agent may be discontinued.

The toluene feedstock preferably includes about 50% to 100% toluene, more preferably at least about 80% toluene in the toluene feedstock. Other compounds such as benzene, xylenes, and trimethylbenzene may also be present in the toluene feedstock without adversely affecting the present invention.

The toluene feedstock may also be dried, if desired, in a manner which will minimize moisture entering the reaction zone. Methods known in the art suitable for drying the toluene charge for the present process are numerous. These methods include percolation through any suitable desiccant, for example, silica gel, activated alumina, molecular sieves or other suitable substances, or the use of liquid charge dryers.

The catalytic molecular sieves for the present invention are preferably in the hydrogen form but may be in the ammonium or sodium form and preferably comprise an intermediate pore-size zeolite such as a ZSM-5, ZSM-11, ZSM-22, ZSM-23, or ZSM-35 as discussed above. The catalyst preferably has an alpha value greater than 100, for example about 150–2000, and a silica-alumina ratio less than 1000 preferably about 20–500. The Alpha Value of the catalyst may be increased by initially treating the catalyst with nitric acid or by mild steaming before pre-selectivation. This type of steaming is discussed in U.S. Pat. No. 4,326,994.

The Alpha Value is an approximate indication of the catalytic cracking activity of the catalyst compared to a standard catalyst and it gives the relative rate constant (rate of normal hexane conversion per volume of catalyst per unit time.) It is based on the activity of the amorphous silica-alumina cracking catalyst taken as an Alpha of 1 (Rate Constant=0.016 sec$^{-1}$). The Alpha Test is described in U.S. Pat. No. 3,354,078 and in *The Journal of Catalysis*, Vol. 4, pp. 522–529 (August 1965): Vol. 6, p. 278 (1966); and Vol. 61, p. 395 (1980), each incorporated herein by reference as to that description. It is noted that intrinsic rate constants for many acid-catalyzed reactions are proportional to the Alpha Value for a particular crystalline silicate catalyst (see "The Active Site of Acidic Aluminosilicate Catalysts," *Nature*, Vol. 309, No. 5959, pp. 589–591, 14 Jun. 1984). The experimental conditions of the test used herein include a constant temperature of 538° C. and a variable flow rate as described in detail in the *Journal of Catalysis*, Vol. 61, p. 395. The catalytic molecular sieves also preferably have a Constraint Index of about 1–12. The method by which Constraint Index is determined is described fully in U.S. Pat. No. 4,016,218, incorporated herein by reference for details of the method. The crystal size of zeolites used herein is preferably greater than 0.1 micron.

For the improved disproportionation process of this invention, the suitable molecular sieve may be employed in combination with a support or binder material such as, for example, a porous inorganic oxide support or a clay binder. While the preferred binder is silica, other non-limiting examples of such binder materials include alumina, zirconia, magnesia, thoria, titania, boria and combinations thereof, generally in the form of dried inorganic oxide gels or gelatinous precipitates. Suitable clay materials include, by way of example, bentonite and kieselguhr. The relative proportion of suitable crystalline molecular sieve to the total composition of catalyst and binder or support may be about 30 to about 90 percent by weight and is preferably about 50–80 percent by weight of the composition. The composition may be in the form of an extrudate, beads or fluidizable microspheres.

Operating conditions employed in the process of the present invention will affect the para-selectivity and toluene conversion rate. Such conditions include the temperature, pressure, space velocity, molar ratio of the reactants, and the hydrogen to hydrocarbon mole ratio. A pre-selectivated and steamed catalytic molecular sieve may be contacted with a toluene feedstock which includes a silicone compound under conditions for effecting vapor-phase disproportionation. Conditions effective for accomplishing the high para-selectivity and acceptable toluene disproportionation conversion rates include a reactor inlet temperature of about 350°–540° C., preferably greater than about 400° C., a pressure of about atmospheric –5000 psig, preferably about 100 to 1000 psig, a WHSV of about 0.1–20, preferably about 2–10, and a hydrogen to hydrocarbon mole ratio of about 0.1–20, preferably about 2–6. This process may be conducted in either batch or fluid bed operation with attendant benefits of either operation readily obtainable. The effluent may be separated and distilled to remove the desired product, i.e., para-xylene, plus other by-products.

The catalyst may be further modified in order to reduce the amount of undesirable by-products, particularly ethylbenzene. The state of the art is such that the reactor effluent from standard toluene disproportionation typically contains about 0.5% ethylbenzene by-product. Upon distillation of the reaction products, the level of ethylbenzene in the $C_8$ fraction often increases to about 3–4 percent. This level of ethylbenzene is unacceptable for polymer grade p-xylene since ethylbenzene in the $C_8$ product, if not removed, degrades the quality of fibers ultimately produced from the p-xylene product. Consequently, ethylbenzene content must be kept low. The specification for ethylbenzene in the $C_8$ product has been determined by industry to be less than 0.3%. Ethylbenzene can be substantially removed by isomerization or by superfractionation processes. Removal of the ethylbenzene by conventional isomerization may be impractical when the xylene stream includes greater than 70 or 80 percent para-xylene, since the para-xylene would be concurrently isomerized to equilibrium xylenes reducing the amount of para-xylene in this xylene stream. It is known in the art that the alternative procedure of removing the ethylbenzene by superfractionation is extremely expensive.

In order to avoid the need for downstream ethylbenzene removal, the level of ethylbenzene by-product is advantageously reduced by incorporating a hydrogenation-dehydrogenation function in the catalyst, such as by addition of a metal compound such as platinum. While platinum is the preferred metal, other metals such as palladium, nickel, copper, cobalt, molybdenum, rhodium, ruthenium, silver, gold, mercury, osmium, iron, zinc, cadmium, and mixtures thereof may be utilized. The metal may be added by cation exchange, in amounts of about 0.01–2%, typically about 0.5%. The metal must be able to enter the pores of the catalyst in order to survive a subsequent calcination step. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. The metallic compound advantageously enters the pores of the catalyst. The catalyst can then be filtered, washed with water and calcined at temperatures of about 250° to 500° C.

The following non-limiting examples illustrate the invention.

In the examples, the o-xylene sorption rate parameter $D_o/r^2$ was measured at 120° C. and 3.9 torr.

$D_o$=diffusivity of o-xylene r=crystal size $D_o/r^2$ = the diffusion rate constant (K) which is the rate that o-xylene diffuses out of the crystal

COMPARATIVE EXAMPLES 1–3

EXAMPLE 1

HZSM-5/Al$_2$O$_3$ was steamed at 342° C. for 3 hours with 100% steam then tested for toluene disproportionation. One atmosphere toluene was reacted with the steamed ZSM-5/Al$_2$O$_3$ at 482° C. and the toluene conversion changed by varying the toluene WHSV. The p-xylene selectivity of the unsteamed catalyst was 37.5% at 4% toluene conversion with a TDP (toluene disproportionation) rate constant (K) of 163. After steaming the p-xylene selectivity decreased to 30.6% at 4% toluene conversion and a TDP rate constant of 341.

EXAMPLES 2–3

Additional samples of HZSM-5/Al$_2$O$_3$ were steamed and tested for toluene disproportionation and TDP rate constant. The results are shown in Table 1.

TABLE 1

|  | Unsteamed | | Steamed | |
| --- | --- | --- | --- | --- |
|  | K | p-sel* | K | p-sel |
| Example 2 | 190 | 35.0 | 363 | 30.0 |
| Example 3 | 176 | 36.9 | 384 | 30.0 |

*p-sel = para selectivity

The results of Examples 1–3 show that steaming a non-pre-selectivated catalyst decreases para-selectivity.

EXAMPLE 4

One gram of water soluble n-propylamine silane polymer was diluted with 1 gram deionized (DI) H$_2$O. One gram of as-synthesized ZSM-5 was mixed with 1 gram of the silane polymer/H$_2$O solution at room temperature for 2 hours. The sample was dried at 130° C. then calcined in nitrogen followed by air at 538° C.

The o-xylene sorption was measured at 120° C. before and after treatment. The D/r$^2$ had decreased from $8.5 \times 10^{-6}$ s$^{-1}$ to $6.5 \times 10^{-7}$ s$^{-1}$.

EXAMPLE 5

A silica modified HZSM-5 catalyst prepared as described in Example 4 was tested for toluene disproportionation. One atmosphere toluene was reacted with the catalyst at 482° C. The conversion was changed by varying the WHSV. 42.9% p-xylene selectivity was obtained at 4% toluene conversion with a rate constant of 105.

EXAMPLE 6

The silica modified HZSM-5 prepared as described in Example 4 was steamed at 342° C. and 100% H$_2$O(g) for three hours. After steaming the sample was tested for toluene disproportionation as in Example 5. 73.2% p-selectivity was obtained at 4% toluene conversion. The steam treatment increased the p-xylene selectivity from 42.9% to 73.2%. The rate constant for toluene disproportionation increased after steaming from 105 to 150. The o-xylene sorption rate parameter, D/r$^2$, had decreased from $6.5 \times 10^{-7}$ s$^{-1}$ to $1.85 \times 10^{-7}$ s$^{-1}$.

EXAMPLE 7

One gram of water soluble n-propylamine silane polymer was diluted with 5 grams deionized water. One gram of HZSM-5/Al$_2$O$_3$ was mixed with 1 gram of the silane polymer/H$_2$O solution at room temperature for 2 hours. The sample was dried at 130° C. then calcined in nitrogen followed by air at 538° C.

The o-xylene sorption parameter was measured before and after silane treatment. The D/r$^2$ decreased from $4.8 \times 10^{-6}$ s$^{-1}$ before treatment to $6.7 \times 10^{-7}$ s$^{-1}$ after treatment.

EXAMPLE 8

The silica modified HZSM-5/Al$_2$O$_3$ prepared in Example 7 was steamed at 342° C. and 100% H$_2$O(g) for three hours. The sample was tested for toluene disproportionation before and after steaming. Steam treatment increased the p-xylene selectivity from 40.5% to 67.9% at 4% toluene conversion. The rate constant for toluene disproportionation (k$_D$) increased after steaming from 91 to 195.

EXAMPLE 9

Ten grams of water soluble n-propylamine silane polymer was diluted with 10 grams deionized (DI) H$_2$O. Five grams of ZSM-5/SiO$_2$ was mixed with five grams of the silane solution at room temperature for 2 hours. The sample was dried at 130° C. then calcined in nitrogen followed by air at 538° C.

The o-xylene sorption rate was measured before and after silane treatment. The $D_o/r^2$ decreased from $1.5 \times 10^{-4}$ s$^{-1}$ before treatment to $9.0 \times 10^{-7}$ s$^{-1}$ after treatment.

EXAMPLE 10

The modified ZSM-5/SiO$_2$ prepared in Example 9 was steamed at 342° C. and 100% H$_2$O (g) for three hours.

The o-xylene sorption rate was measured. The $D_o/r^2$ decreased from $9.0 \times 10^{-7}$ s$^{-1}$ before treatment to $5.6 \times 10^{-7}$ s$^{-1}$ after treatment.

EXAMPLE 11

A silica modified ZSM-5/SiO$_2$ catalyst prepared as described in U.S. Pat. No. 4,090,981 was steamed at 342° C. for 3 hours with 100% steam. The catalyst was tested before and after steaming. At 446° C., 8 WHSV, 2 H$_2$/HC and 500 psi, the steamed silica modified ZSM-5/SiO$_2$ showed 93.4% p-xylene selectivity at 18.9% toluene conversion while the unsteamed catalyst showed 79.2% p-xylene selectivity at 18.3% toluene conversion.

EXAMPLE 12

A silica modified ZSM-5/Al$_2$O$_3$ catalyst prepared as described in U.S. Pat. No. 4,090,981 was steamed at 342° C. for 3 hours with 100% steam. After steaming, the sample was tested for toluene disproportionation as described in Example 5. After steaming, the p-xylene selectivity increased from 60.6% to 86.7% at 4% toluene conversion. The rate constant for toluene disproportionation increased from 149 to 238.

EXAMPLE 13

NaZSM-5/SiO$_2$ was treated with a propylamine silane polymer/H$_2$O mixture, 7:1 wt ratio, at room temperature for overnight. The sample was filtered and dried at 130° C. and then calcined at 538° C. in nitrogen followed by air.

The calcined sample was exchanged 2–3 times with 1M NH$_3$NO$_3$ at room temperature for 1–2 hours. The o-xylene diffusivity was 3×10$^{-7}$ s$^{-1}$. NH$_3$-TPAD was performed to determine the number of acid sites which was 0.43 meq/g.

The exchanged SiO$_2$-ZSM-5/SiO$_2$ material was calcined in air at 538° C. and then steamed at 315° C. for 3 hours in 100% steam.

Catalytic evaluation of selectivated-steamed catalyst was conducted in an automated unit with on line sampling. One gram of 14/30 mesh steamed material was loaded into a 0.305" stainless steel tube reactor. The sample was heated to 446° C. in 40 cc/min H$_2$ at a heating rate of 3.5° C./min. Pure toluene was then introduced at 446° C., 4, 8, 16 and 32 WHSV, 2 H$_2$/HC and 500 psi to measure the catalytic performance. A solution of 1 wt. % phenylmethyl-dimethyl silicone copolymer (Dow 550) in toluene was then passed over the catalyst at 466° C., 4 WHSV, 2 H$_2$/HC and 500 psi for 4 hours. To determine the activity/selectivity performance of the selectivated catalysts, reactor temperature was varied to change toluene conversion. Toluene conversion/p-xylene selectivities are shown below in Table 2.

TABLE 2

| Temp, °C. | 446 | 466 |
|---|---|---|
| WHSV | 4 | 4 |
| Pres, psi | 500 | 500 |
| H$_2$/HC | 2 | 2 |
| Toluene Conv., % | 15.5 | 27.1 |
| p-xylene sel., % | 96.9 | 91.4 |

EXAMPLE 14 a. Five grams of propylamine silane polymer were diluted with 5 grams DI H$_2$O. 10 grams of Na-ZSM-5/SiO$_2$ were treated with 10 grams of the propylamine silane polymer/H$_2$O solution by impregnation for overnight and then dried at 130° C.

The sample was then calcined in 300 cc/min N$_2$ using a heating rate of 2° C./min to 538° C. then held at 538° C. for 2 hours followed by 300 cc/min air heated at 2° C./min from 300° C. to 538° C. then held for 2 hours.

The o-xylene diffusivity was measured at 120° C. The selectivation procedure reduced the D/r$^2$ from 1.5×10$^{-4}$ s$^{-1}$ to 1×10$^{-5}$ s$^{-1}$. To reduce the diffusivity further a second selectivation was performed.

b. 7 grams of propylamine silane polymer were diluted with 3 grams DI H$_2$O. 10 grams of SiO$_2$//Na-ZSM-5/SiO$_2$ described in a. above were treated with 10 grams of the propylamine silane polymer/H$_2$O solution by impregnation for overnight and then dried at 130° C. The sample was N$_2$/air calcined as described above.

The calcined sample was exchanged 2–3 times with 1M NH$_4$NO$_3$ at room temperature for 1–2 hours to reduce the sodium content to less than 500 ppm. The sample was calcined in air at 538° C. for 2 hours then steamed at 343° C. in 100% steam. Representative catalyst selectivities are shown below after 6 hours trim selectivation with 1% methylphenyl-dimethylsilicone in toluene was then passed over the catalyst at 466° C., 4 WHSV, 2 H$_2$/HC and 500 psi for 6 hours. Toluene conversion/p-xylene selectivities are shown in Table 3.

TABLE 3

| Temp, °C. | 466 | 446 |
|---|---|---|
| WHSV | 4 | 8 |
| Pres, psi | 500 | 500 |
| H$_2$/HC | 2 | 2 |
| Toluene Conv., % | 30.9 | 17.1 |
| p-xylene sel., % | 90.2 | 93.5 |

What is claimed is:

1. A method for modifying a catalytic molecular sieve comprising pre-selectivating the molecular sieve with a first silicon-containing compound selected from the group consisting of silicones, tetraalkoxy silanes, and organoamine silane polymers, calcining and subsequently steaming at about 200° C. to about 400° C.

2. A method of claim 1 wherein the molecular sieve comprises a zeolite having an initial Constraint Index of from about 1 to about 12.

3. The method of claim 1 wherein the molecular sieve is incorporated with binder before being modified.

4. The method of claim 1 wherein the molecular sieve is incorporated with binder after being modified.

5. The method of claim 1 wherein the silicon-containing compound is selected from the group consisting of Si(OR)$_4$, wherein R is selected from the group consisting of CH$_3$, C$_2$H$_5$ and C$_3$H$_7$;

(SiO(R')$_2$)$_n$, wherein R' is selected from the group consisting of alkyl of C$_{1-10}$, aryl of C$_{6-10}$, hydroxide and hydrogen and n is greater than 10 and less than 1000; and organoamine silane polymer, wherein the organoamine is selected from the group consisting of —N(CH$_3$)$_3$, —N(C$_2$H$_5$)$_3$ and —N(C$_3$H$_7$)$_3$.

6. The method of claim 1 wherein the steaming comprises treating the molecular sieve with steam under conditions comprising between about five and about 100 percent water vapor, and a pressure of from about 0.1 to about 50 psig, for a time of about two to about 12 hours.

7. The method of claim 1 wherein the molecular sieve is modified in an as-synthesized condition.

8. The method of claim 1 further comprising contacting the pre-selectivated calcined, steamed catalytic molecular sieve with a mixture comprising toluene and a second silicon source which is a, paraxylene selectivating agent at reaction conditions for convening toluene to xylene for at least one hour to yield a twice modified molecular sieve.

9. The method of claim 8 wherein the second silicon source is a silicone.

10. The method of claim 9 wherein the silicone comprises a mixture of phenylmethylsilicone and dimethylsilicone.

11. A catalyst comprising:

a molecular sieve having an initial Constraint Index of about 1–12 which has been modified by being (i) pre-selectivated by contacting with a first silicon source selected from the group consisting of silicones, tetraalkoxy silanes and organoamine silane polymers, calcined, and (ii) treated with steam at about 280° C. about 400° C.;

so that para-substituted aromatic product selectivity of the catalyst is increased over meta- and ortho-substituted aromatic product.

12. The catalyst of claim 11 wherein the pre-selectivated, calcined, steam treated molecular sieve is subsequently contacted with a mixture comprising toluene and a second silicon source which is a paraxylene selectivation agent at reaction conditions for converting toluene to xylene for at least one hour to yield a twice modified catalyst.

\* \* \* \* \*